United States Patent
Magara et al.

(10) Patent No.: US 6,177,067 B1
(45) Date of Patent: Jan. 23, 2001

(54) HAIR REVITALIZING TONIC COMPOSITION CONTAINING A 2,2-DIMETHYLPROPANEDIOL COMPOUND AND USE THEREOF

(75) Inventors: Tsunao Magara, Tokyo; Yoshiharu Tsuji, Atami; Masahiro Tajima, Yokohama; Koji Kobayashi, Kasugai; Hirotada Fukunishi, Yokohama; Masazumi Watanabe, Kawanishi, all of (JP)

(73) Assignees: Shiseido Company, Ltd., Tokyo; Takeda Chemical Industries, Ltd., Osaka, both of (JP)

( * ) Notice: Under 35 U.S.C. 154(b), the term of this patent shall be extended for 0 days.

(21) Appl. No.: 09/169,940

(22) Filed: Oct. 13, 1998

Related U.S. Application Data

(63) Continuation-in-part of application No. 08/911,350, filed on Aug. 7, 1997, now abandoned.

(30) Foreign Application Priority Data

Aug. 9, 1996 (JP) .................................................. 8-226139

(51) Int. Cl.$^7$ .................................................. A61K 7/06
(52) U.S. Cl. ..................... 424/70.1; 424/70.11; 424/401; 514/231.2; 514/235.8; 514/238.8; 514/239.2; 514/255; 514/315; 514/483; 514/553; 514/880; 132/202; 560/115
(58) Field of Search .................. 132/202; 514/315, 514/880, 231.2, 235.8, 238.8, 239.2, 255, 483, 553; 560/115; 424/70.11, 401, 70.1

(56) References Cited

U.S. PATENT DOCUMENTS

| | | | |
|---|---|---|---|
| 2,937,119 | 5/1960 | Berger et al. ........................ | 560/166 |
| 3,344,170 | 9/1967 | Strycker ................................ | 260/482 |
| 4,255,310 | 3/1981 | Oppenlaender et al. ............. | 260/29.6 |
| 4,596,812 | * 6/1986 | Chidsey et al. ...................... | 514/256 |
| 4,737,518 | 4/1988 | Nomura et al. ...................... | 514/476 |
| 5,089,269 | 2/1992 | Noda et al. ........................... | 424/456 |
| 5,185,334 | 2/1993 | Soloman et al. .................. | 514/236.2 |
| 5,354,510 | 10/1994 | Vanlerberghe et al. .............. | 252/548 |
| 5,371,252 | 12/1994 | Zysman et al. ...................... | 554/109 |
| 5,431,905 | 7/1995 | Zysman et al. ...................... | 424/70.8 |
| 5,618,798 | * 4/1997 | Bar-Shalom et al. ................ | 514/53 |
| 5,877,184 | * 3/1999 | Sinclair ................................ | 514/291 |

FOREIGN PATENT DOCUMENTS

| | | |
|---|---|---|
| 142 333 | 5/1985 | (EP) . |
| 157 609 | 10/1985 | (EP) . |
| 254 540 | 1/1988 | (EP) . |
| 301 751 | 2/1989 | (EP) . |
| 353 474 | 2/1990 | (EP) . |
| 420 761 | 4/1991 | (EP) . |
| 577 506 | 1/1994 | (EP) . |
| 666 251 | 8/1995 | (EP) . |
| 811 370 | 12/1997 | (EP) . |
| 2627384 | 8/1989 | (FR) . |
| 1-104036 | 3/1988 | (JP) . |
| 2-129110 | 5/1990 | (JP) . |
| WO89/07100 | 8/1989 | (WO) . |

OTHER PUBLICATIONS

CAS 119:203999, Belgacem et al., 1993.

\* cited by examiner

*Primary Examiner*—Christopher S. F. Low
*Assistant Examiner*—Anish Gupta
(74) *Attorney, Agent, or Firm*—Wenderoth, Lind & Ponack, L.L.P.

(57) ABSTRACT

Disclosed is a hair revitalizing tonic composition containing a dimethylpropanediol derivative of the formula:

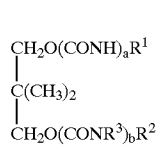

(I)

wherein $R^1$ and $R^2$ are each independently a $C_{1-30}$ hydrocarbon group which may be substituted, or a five- or six-membered heterocyclic group which contains 1 to 4 heteroatoms selected from oxygen, sulfur and nitrogen atoms and which may be substituted, $R^3$ is hydrogen atom, an alkyl group which may be substituted, an acyl group, an alkoxycarbonyl group, a phenoxycarbonyl group, or a carbamoyl group which may be substituted, and a and b are each 0 or 1, as well as a method for effecting hair growth promotion, hair growth stimulation, or hair loss prevention in mammals by using such a hair revitalizing tonic composition. Also disclosed is the use of a compound of formula (I) in the preparation of a hair revitalizing tonic composition. Thus, this invention can provide an excellent means of hair revitalization or hair loss prevention in mammals.

19 Claims, No Drawings

HAIR REVITALIZING TONIC COMPOSITION CONTAINING A 2,2-DIMETHYLPROPANEDIOL COMPOUND AND USE THEREOF

This is a Continuation-In-Part of U.S. patent application Ser. No. 08/911,350 filed Aug. 7, 1997, now abandoned.

BACKGROUND OF THE INVENTION

This invention relates to the hair revitalization of mammals and, more particularly, to the use of novel 2,2-dimethylpropanediol derivatives for purposes of hair revitalization.

Conventionally, hair revitalizing tonic compositions containing various components such as certain vitamins, amino acids, female hormones, and plant extracts having a vasodilative effect or an anti-inflammatory effect have been used for the prophylaxis and treatment of alopecia or, prevention or treatment of hair loss. Moreover, a variety of other compounds have also been proposed for use as active ingredients, but they are not always satisfactory from the viewpoint of efficacy. Meanwhile, a large number of 2-substituted glycerol derivatives having antiallergic and anti-inflammatory effects have been synthesized (see, for example, Published Japanese Translation of PCT International Publication No. 501612/'91), and much attention is focused on their excellent effects.

However, there is a still continuing need for a more excellent hair revitalizing tonic composition. Accordingly, it is an object of the present invention to provide a hair revitalizing tonic composition containing, among others, a chemically synthesized compound having a hair growth promotion or stimulation effect, as well as the use of such a compound in a hair revitalizing method.

SUMMARY OF THE INVENTION

The present inventors have synthesized various compounds and examined their hair growth promotion effects. As a result, it has now been found that novel dimethylpropanediol derivatives having two methyl groups at the 2-position have an excellent hair growth promotion effect.

According to the present invention, there is provided a hair revitalizing tonic composition comprising a novel 2,2-dimethylpropanediol derivative of the following formula (I) or a salt thereof which is present in an amount effective for the hair revitalization of mammals, together with a pharmaceutically or cosmetically acceptable vehicle or other component.

Formula (I):

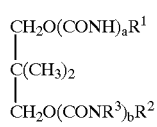

wherein $R^1$ and $R^2$ are each independently a $C_{1-30}$ hydrocarbon group which is optionally substituted, or a five- or six-membered heterocyclic group which contains 1 to 4 heteroatoms selected from oxygen, sulfur and nitrogen atoms and which is optionally substituted, $R^3$ is hydrogen, an alkyl group which is optionally substituted, an acyl group, an alkoxycarbonyl group, a phenoxycarbonyl group, or a carbamoyl group which is optionally substituted, and a and b are each independently 0 or 1.

According to another feature of the present invention, there is provided a hair revitalizing method for mammals which comprises topically applying a compound of formula (I) or a pharmaceutically or cosmetically acceptable salt thereof to the skin or hair of a mammal.

Furthermore, there is provided the use of a compound of formula (I) in the preparation of a hair revitalizing tonic composition as described above.

The compounds represented by the above formula (I) and salts thereof exhibit a significantly excellent hair growth promotion effect and, moreover, a hair loss prevention effect and a dandruff and itchy scalp suppression effect. Accordingly, the term "hair revitalization" or "hair revitalizing action" as used herein means at least one of the above-described effects.

DETAILED DESCRIPTION OF THE INVENTION

The compounds of formula (I) are more specifically described hereinbelow.

The $C_{1-30}$ hydrocarbon groups represented by $R^1$ and $R^2$ in formula (I) include, for example, $C_{1-30}$ alkyl groups, $C_{3-8}$ cycloalkyl groups, $C_{2-10}$ alkenyl groups, $C_{2-10}$ alkynyl groups, $C_{3-10}$ cycloalkenyl groups, $C_{6-14}$ aryl groups and $C_{7-16}$ aralkyl groups.

Examples of the $C_{1-30}$ alkyl groups include straight-chain alkyl groups such as methyl, ethyl, butyl, pentyl, hexyl, heptyl, octyl, nonyl, decyl, undecyl, dodecyl, tridecyl, tetradecyl, pentadecyl, hexadecyl, heptadecyl, octadecyl, nonadecyl, icosyl, henicosyl, docosyl, tricosyl, tetracosyl, pentacosyl, hexacosyl, heptacosyl, octacosyl, nonacosyl and triacontyl; and branched alkyl groups such as isopropyl, isobutyl, sec-butyl, tert-butyl, 2-methylpentyl, 3-methylpentyl, 4-isocapryl, 4-ethylpentyl, 6-methyldecyl, 9-methyldecyl, 6-ethylnonyl, 5-propyloctyl, 11-methyldodecyl, 12-methyldodecyl, 4-methyltetradecyl, 13-methyltetradecyl, 14-ethylhexadecyl, 10-methyloctadecyl, 15-ethylpentadecyl, 10-methyidocosyl, 2-pentyloctadecyl, 22-methyltricosyl, 12-hexyloctadecyl, 6-methyltetracosyl, 24-methylheptacosyl, 2-decylhexadecyl, 2-nonyloctadecyl, 2-dodecyloctadecyl, 3-methyltetracosyl and 3-methyltricosyl.

Preferred examples of the groups represented by $R^1$ and $R^2$ are straight-chain or branched $C_{6-30}$ alkyl groups which are optionally substituted, and more preferred examples thereof are straight-chain or branched $C_{6-22}$ alkyl groups, or more preferred examples thereof are straight-chain or branched $C_{8-20}$ or $C_{12-25}$ alkyl groups.

Examples of the $C_{3-8}$ cycloalkyl groups include cyclopropyl, cyclopentyl and cyclohexyl. Examples of the $C_{2-10}$ alkenyl groups include vinyl, allyl, 2-methylallyl, 2-butenyl, 3-butenyl, 3-octenyl, 2-nonenyl and 4-decenyl. Examples of the $C_{2-10}$ alkynyl groups include ethynyl, 2-propynyl and 3-hexynyl.

Examples of the $C_{3-10}$ cycloalkenyl groups include cyclopropenyl, cyclopentenyl and cyclohexenyl. Examples of the $C_{6-14}$ aryl groups include phenyl and naphthyl. Examples of the $C_{7-16}$ aralkyl groups include benzyl, phenylethyl and naphthylethyl.

The foregoing groups represented by $R^1$ and $R^2$ may have one or more (e.g., one to five) substituents at any substitutable position or positions in the carbon chain or carbon ring. Specific examples of the substituents include halogen (e.g., fluorine, chlorine, bromine and iodine) and $C_{3-8}$ cycloalkyl, hydroxyl, mercapto, oxo, thioxo, cyano, carbamoyl, carboxyl, $C_{1-4}$ alkoxycarbonyl (e.g., methoxycarbonyl and ethoxycarbonyl), sulfo, $C_{1-4}$ alkoxy (e.g., methoxy, ethoxy, propoxy, isopropoxy, butoxy, isobutoxy, sec-butoxy and tertbutoxy), phenoxy, halogenophenoxy (e.g., o-, m- or p-chlorophenoxy and o-, m- or p-bromophenoxy), lower ($C_{1-4}$) alkylthio (e.g., methylthio, ethylthio, n-propylthio, isopropylthio, n-butylthio and tert-butylthio), phenylthio, $C_{1-4}$ alkylsulfinyl (e.g., methylsulfinyl and ethylsulfinyl), $C_{1-4}$ alkylsulfonyl (e.g., methylsulfonyl and ethylsulfonyl) and $C_{1-10}$ loalkyl groups (e.g., difluoromethyl, trifluoromethyl, trifluoroethyl and trichloroethyl). Other specific examples of the substituents for the hydrocarbon groups include amino; substituted amino such as $C_{1-6}$ acylamino (e.g., acetylamino and propionylamino), $C_{1-30}$ alkylamino (e.g., methylamino, ethylamino, n-propylamino, isopropylamino, n-butylamino, isobutylamino, s-butylamino, t-butylamino, pentylamino, hexylamino, heptylamino, octylamino, nonylamino, decylamino, undecylamino, dodecylamino, tridecylamino, tetradecylamino, pentadecylamino, hexadecylamino, heptadecylamino, octadecylamino, nonadecylamino, icosylamino, henicosylamino, docosylamino, tricosylamino, tetracosylamino, pentacosylamino, hexacosylamino, heptacosylamino, octacosylamino, nonacosylamino and triacontylamino), di-$C_{1-4}$ alkylamino-(e.g., dimethylamino, diethylamino, N-methyl-N-ethylamino and N-methyl-N-propylamino); $C_{1-5}$ acyl (e.g., $C_{1-5}$ alkanoyl such as formyl, acetyl and propionyl); and benzoyl group.

Further specific examples of the substituents for the hydrocarbon groups include five- and six-membered heterocyclic groups which contain 1 to 4 heteroatoms selected from oxygen, sulfur and nitrogen atoms and which are optionally substituted, such as pyrrolidyl, piperidyl, morpholino, thiomorpholino, 2- or 3-thienyl, 2- or 3-furyl, 3-, 4- or 5-pyrazolyl, 2-, 4- or 5-thiazolyl, 3-, 4- or 5-isothiazolyl, 2-, 4- or 5-oxazolyl, 3-, 4- or 5-isoxazolyl, 2-, 4- or 5-imidazolyl, 1,2,3- or 1,2,4-triazolyl, 1H- or 2H-tetrazolyl, 2-, 3- or 4-pyridyl, 2-, 4- or 5-pyrimidyl, 3- or 4-pyridazinyl, quinolyl, imidazoquinolyl and indolyl.

These heterocyclic groups are usually linked to $C_{1-2}$ hydrocarbon groups. These heterocyclic groups may have 1 to 4 substituents. Specific examples of these substituents include halogen (e.g., fluorine, chlorine and bromine), $C_{1-4}$ alkyl groups (e.g., methyl, ethyl, propyl and isopropyl) and halogenophenoxy (e.g., o-, m- or p-chlorophenoxy and o-, m- or p-bromophenoxy).

Preferred substituents for the aforesaid cycloalkyl, cycloalkenyl, aryl and aralkyl groups include $C_{1-4}$ alkyl groups such as methyl, ethyl, propyl, isopropyl and butyl, and they may have one to four substituents selected from such alkyl groups. Where the aforesaid alkyl groups are substituted by a $C_{3-8}$ cycloalkyl group or groups, it is preferable that the alkyl groups are straight-chain $C_{6-14}$ alkyl groups.

Examples of the heterocyclic groups represented by $R^1$ and $R^2$ include the same five- and six-membered heterocyclic groups which contain 1 to 4 heteroatoms selected from oxygen, sulfur and nitrogen atoms as those mentioned above as the substituents for the hydrocarbon groups represented by $R^1$ and $R^2$ Preferred examples of the heterocyclic groups represented by $R^1$ and $R^2$ include five- or six-membered aromatic heterocyclic groups and alicyclic heterocyclic groups, such as 2-, 3- or 4-pyridyl and 2-, 3- or 4-piperidyl. These heterocyclic groups are optionally substituted, preferably by 1 to 4 substituents selected from halogen atoms and $C_{1-4}$ alkyl groups.

Especially preferred compounds are those in which, among the foregoing $R^1$ and $R^2$ groups, $R^1$ is a $C_{1-30}$ hydrocarbon group and $R^2$ is a $C_{1-30}$ hydrocarbon group substituted by an amino group that may be substituted, or salts thereof. In particular, the compounds in which $R^2$ is a group of the formula

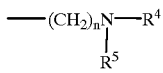

wherein $R^4$ and $R^5$ are each independently a hydrogen atom or a $C_{1-5}$ alkyl group which is optionally substituted, and n is an integer of 1 to 10, or salts thereof are preferred. It is preferable that $R^4$ and $R^5$ represent $C_{1-3}$ alkyl groups which may be the same or different.

Useful substituents for the $C_{1-5}$ alkyl group include, for example, hydroxyl. The $C_{1-5}$ alkyl group may further have 1 to 3 substituents.

In the above formula, $R^4$ and $R^5$ may form a nitrogen-containing heterocyclic ring in conjunction with the nitrogen atom to which they are linked. Specifically, $R^4$ and $R^5$ may be combined to form a tetramethylene or pentamethylene chain. Alternatively, $R^4$ and $R^5$ may form a five- or six-membered heterocyclic ring through the medium of the adjacent nitrogen atom and one or more other heteroatoms (e.g., oxygen, nitrogen and/or sulfur atoms). Among the heterocyclic rings so formed,

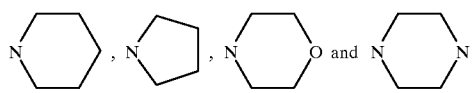

are especially preferred.

In the above formula, examples of the alkyl group represented by $R^3$ include $C_{1-5}$ alkyl groups such as methyl, ethyl, propyl, butyl and pentyl. These alkyl groups are optionally substituted, for example, by 1 to 4 substituents selected from carboxyl and lower ($C_{1-5}$) alkoxycarbonyl (e.g., methoxycarbonyl, ethoxycarbonyl, propoxycarbonyl, butoxycarbonyl or pentoxycarbonyl) groups. Examples of the acyl group represented by $R^3$ include lower ($C_{1-5}$) alkanoyl (e.g., formyl, acetyl, propionyl, butyryl, isobutyryl, valeryl and isovaleryl) and benzoyl. Examples of the alkoxycarbonyl group represented by $R^3$ include methoxycarbonyl, ethoxycarbonyl, propoxycarbonyl, butoxycarbonyl and pentoxycarbonyl. Examples of the carbamoyl group which is optionally substituted as represented by $R^3$, include carbamoyl, lower ($C_{1-5}$) alkylcarbamoyl (e.g., methylcarbamoyl, ethylcarbamoyl, propylcarbamoyl and butylcarbamoyl), di-lower ($C_{1-5}$) alkylcarbamoyl (e.g., dimethylcarbamoyl, methylethylcarbamoyl, diethylcarbamoyl and methylpropylcarbamoyl), three- to seven-membered cyclic aminocarbonyl [e.g., (aziridin-1-yl)carbonyl, (azetidin-1-yl)carbonyl, (pyrrolidin-1-yl)carbonyl, piperidinocarbonyl, (piperazin-1-yl)carbonyl, morpholinocarbonyl and thiomorpholinocarbonyl].

The alkyl group represented by $R^3$ may be combined with $R^4$ or $R^5$ to form an alkenylene or alkylene bridge. Specific examples of the alkenylene or alkylene bridge include lower ($C_{1-4}$) alkenylene and alkylene groups such as methylene, ethylene, trimethylene, tetramethylene, vinylene and propenylene. These groups may have one or two substituents (e.g., oxo) at a substitutable position or positions. Examples of substituted alkylene and alkenylene groups include 1-oxoethylene, 3-oxopropenylene and 1,2-dioxoethylene. In this case, specific examples of the groups which $R^3$ forms in conjunction with $R^4$ or $R^5$ together with the adjacent nitrogen atom include groups of the formulae

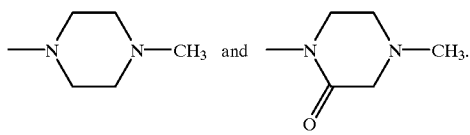

Preferably, $R^3$ is hydrogen or lower alkanoyl. More preferably, $R^3$ is hydrogen.

When both of a and b are 0, the compounds of formula (I) are such that $R^1$ and $R^2$ are each joined through the medium of an ether linkage. When both of a and b are 1, $R^1$ and $R^2$ are joined through the medium of an oxycarbamoyl linkage (—OCONH—) and —OCONR$^3$—, respectively. The compounds in which one of a and b is 0 and the other is 1 also fall within the scope of formula (I). When the compounds of formula (I) have asynmetric carbon atoms in $R^1$ or $R^2$, the compounds may be in optically active forms or in a mixture of optically active forms. Also, the compounds of formula (I) may be hydrates or not be hydrates.

Where the compounds of formula (I) have a basic group such as an amino or imino group, the compounds of formula (I) can be acid addition salts thereof. Such salts include pharmaceutically or cosmetically acceptable inorganic acid salts such as hydrohalogenides (e.g., hydrochloride and hydrobromide), sulfate, nitrate and phosphate; and pharmaceutically or cosmetically acceptable organic acid salts such as acetate, propionate, hydroxyacetate, 2-hydroxypropionate, 2-oxopropionate, ethanedicarboxylate, propanedicarboxylate, butanedicarboxylate, methanesulfonate, ethanesulfonate, benzenesulfonate, 4-methylbenzenesulfonate and 2-hydroxybenzoate. Where the compounds of formula (I) have a carboxyl group, it can also be used as ammonium salts, alkali metal salts (e.g., lithium, sodium and potassium salts), or salts with organic bases (e.g., amino acids such as arginine and lysine).

Compounds (I) or salts thereof (hereinafter, sometimes referred to simply as compounds (I) including compounds (I) and their salts) may be prepared, for example, in the following manner.

A) Compounds (I) can be obtained by reacting a compound (II) of the formula

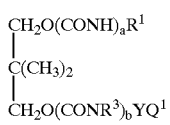
(II)

wherein Y is a $C_{1-30}$ alkylene group which is optionally substituted, $Q^1$ is a group capable of being easily replaced by nitrogen [such as halogen (e.g., chlorine, bromine or iodine), O-tosyl or O-mesyl], and the other symbols are as defined previously, with an amine (III) of the formula

 (III)

wherein the symbols are as defined previously, which are optionally substituted. This reaction may be carried out by adding an equivalent amount or a large excess of compound (III) to compound (II), and reacting this mixture in the presence or absence of a solvent at a temperature of 0 to 200° C. for about 0.5–48 hours. Usable solvents include toluene, benzene, ether, dioxane, tetrahydrofuran and the like, and compound (III) itself may be used as the solvent. Under heated conditions, the reaction may be carried out in a sealed tube.

B) Compounds (I) can be obtained by reacting a compound (IV) of the formula

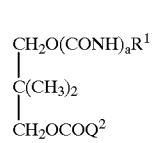
(IV)

wherein $Q^2$ is a group capable of activating the carbonyl group [such as halogen (e.g., chlorine) or phenoxy] and the other symbols are as defined previously, with a compound (V) of the formula $$HN(R^3)—R^2 \quad (V)$$

wherein $R^2$ is as defined above, including a typical group —W—Z (wherein W is a single bond or a lower alkylene group, Z is a mono- or di-substituted amino group or, when W is a single bond, a five- or six-membered nitrogen-containing heterocyclic group joined to a carbon atom), and the other symbol is as defined previously. Examples of the mono- or di-substituted amino groups represented by Z include the same ones as described for the substituted amino group as the substituents for the hydrocarbon groups represented by $R^1$ and $R^2$. The reaction of compound (IV) with compound (V) may be carried out in the presence or absence of a solvent at a temperature of −10 to 150° C. for about 0.5–48 hours. Usable solvents include toluene, benzene, ether, dioxane, tetrahydrofuran, chloroform and the like. In order to accelerate the reaction, a base such as triethylamine or pyridine may be added. It is also possible to react compound (V) with sodium hydride, n-butyllithium or the like in any of the above-described solvents to convert it into a metallic salt thereof, and then react this metallic salt with compound (IV).

C) Compounds (I) can be obtained by reacting a compound (VI) of the formula

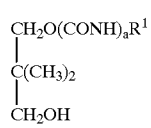
(VI)

wherein the symbols are as defined previously, with a compound (VII) of the formula $$Q^2—CO—N(R^3)—R^2 \quad (VII)$$

wherein the symbols are as defined previously.

In the formula (VII), $R^2$ includes the group —W—Z (wherein the symbols are as defined above).

The reaction of compound (VI) with compound (VII) may be carried out in substantially the same manner as described for the reaction of compound (IV) with compound (V) in B).

D) Compounds of formula (I) in which b is 0 and $R^2$ is —(CH$_2$)$_n$NR$^4$R$^5$ can be obtained by reacting a compound (VIII) of the formula $$\begin{array}{c} CH_2O(CONH)_aR^1 \\ | \\ C(CH_3)_2 \\ | \\ CH_2O(CH_2)_nQ^1 \end{array} \quad \text{(VIII)}$$

wherein the symbols are as defined previously, with a compound (III) of the formula $$NHR^4R^5 \quad \text{(III)}$$

wherein $R^4$ and $R^5$ are as defined previously. This reaction may be carried out in substantially the same manner as described for the reaction of compound (II) with compound (III) in A).

E) Compounds (I) can be obtained by reacting a compound of the formula $$R^2NCO \quad \text{(IX)}$$

wherein the symbol is as defined previously, with a compound of formula (VI). This reaction may be carried out in the presence or absence of a solvent at a temperature of −10 to +150° C. for about 0.5–48 hours. Usable solvents include toluene, benzene, ether, dioxane, tetrahydrofuran, chloroform and the like. In order to accelerate the reaction, a base such as triethylamine, pyridine or 4-dimethylaminopyridine may be added.

Compound (IX) may readily be synthesized, for example, by reacting a compound (X) of the formula $$R^2NH_2 \quad \text{(X)}$$

wherein the symbol is as defined previously, with diphosgene in the absence of solvent or in an inert solvent such as methylene chloride, chloroform, benzene or tetrahydrofuran, at a temperature of −20 to 120° C. for about 0.5–12 hours, or by reacting a compound (XI) of the formula $$R^2COOH \quad \text{(XI)}$$

wherein the symbol is as defined previously, with Diphenyl phospharylazide (DPPA) in a solvent such as chloroform, toluene, benzene, dichloromethane or tetrahydrofuran, in the presence of a tertiary amine such as triethylamine or tributylamine, at a temperature of 0 to 150° C. for about 0.5–48 hours, and then in the presence of a tertiary amine such as pyridine, at a temperature of 0 to 150° C. for about 0.5–48 hours.

A compound of formula (I) in which the nitrogen atom contained in the $R^2$ substituent group is secondary or tertiary can be obtained by reacting a compound of formula (I) in which the nitrogen atom contained in the $R^2$ substituent group is primary or secondary, for example, with an alkyl halide. This reaction may be carried out in a solvent such as ether, chloroform, tetrahydrofuran, benzene or toluene, in the presence of an equivalent amount or large excess of an alkyl halide, at a temperature of 0 to 150° C. for about 0.5–60 hours.

The synthesis intermediate (VIII) can be obtained, for example, by reacting a compound (VI) of the formula $$\begin{array}{c} CH_2O(CONH)_aR^1 \\ | \\ C(CH_3)_2 \\ | \\ CH_2OH \end{array} \quad \text{(VI)}$$

wherein the symbols are as defined previously, with a dihaloalkane of the formula $$Hal(CH_2)_nHal \quad \text{(XII)}$$

wherein Hal represents a halogen atom such as chlorine and bromine, and the other symbols are as defined above. This reaction may be carried out in the absence of solvent or in a suitable solvent (e.g., benzene, toluene, hexane, dioxane or tetrahydrofuran), in the presence of a strong base (e.g., sodium hydroxide, potassium hydroxide or an aqueous solution thereof) and preferably in the presence of a phase-transfer catalyst (e.g., cetyltrimethylammonium chloride or benzyltrimethylammonium chloride) under water-containing conditions, at a temperature of −20 to 150° C. and preferably 20 to +100° C. for about 0.5–60 hours.

The starting compound (VI) may be prepared according to the following reaction formula.

$$\begin{array}{c} CH_2OH \\ | \\ C(CH_3)_2 \\ | \\ CH_2OH \end{array} \xrightarrow[\text{(when a is 1)}]{\begin{array}{c} R^1NCO \\ (XIV) \end{array}} \text{or} \xrightarrow[\text{(when a is 0)}]{\begin{array}{c} R^1-Hal \\ (XV) \end{array}} \begin{array}{c} CH_2O(CONH)_aR^1 \\ | \\ C(CH_3)_2 \\ | \\ CH_2OH \end{array}$$

(XIII)                                              (VI)

wherein the symbols are as defined previously.

The reaction of compound (XIII) with alkyl isocyanate (XIV) may be carried out in the presence or absence of a solvent at a temperature of −10 to +150° C. for about 0.5–48 hours. Usable solvents include toluene, benzene, ether, dioxane, tetrahydrofuran, chloroform and the like. In order to accelerate the reaction, a base such as triethylamine, pyridine or 4-dimethylaminopyridine may be added. The reaction of compound (XIII) with alkyl halide (XV) may be carried out in substantially the same manner as described for the reaction of compound (VI) with compound (XII).

In this reaction, a compound (XVI) of the formula $$\begin{array}{c} CH_2O(CONH)_aR^1 \\ | \\ C(CH_3)_2 \\ | \\ CH_2O(CONH)_aR^1 \end{array} \quad \text{(XVI)}$$

wherein the symbols are as defined previously, [i.e., a compound of formula (I) in which $R^1$ and $R^2$ are the same, a and b are the same, and $R^3$ is hydrogen] can be obtained by reacting one mole of the starting compound (XIII) with two or more moles of compound (XIV) or (XV).

The starting compound (IV) can be produced by reacting compound (VI) with phenyl halogenocarbonate (e.g., phenyl chlorocarbonate) in accordance with the similar reaction conditions as described for the production method E).

In each of the above-mentioned reactions, when the starting compounds and intermediate compounds has amino group, carboxyl group or hydroxyl group as the substituent, they may have a protective group generally used in the peptide chemistry. After completion of the reaction, the target compound can be obtained by removing the protective group upon necessity.

Examples of the amino-protecting group include optionally substituted $C_{1-6}$ alkyl carbonyl (e.g, formyl, methyl carbonyl and ethyl carbonyl), phenyl carbonyl, $C_{1-6}$ alkyl-oxycarbonyl (e.g. methoxycarbonyl and ethoxycarbonyl), phenyloxycarbonyl (e.g. benzoxycarbonyl), $C_{7-10}$ aralkyloxy-carbonyl (e.g. benzyloxycarbonyl), trityl and phthaloyl. Examples of substituents of them include halogen atoms (e.g. fluoro, chloro, bromo and iodo), $C_{1-6}$ alkyl-carbonyl (e.g. methylcarbonyl, ethylcarbonyl and butylcarbonyl) and nitro group, and the number of the substituents ranges from about 1 to 3.

Examples of the carboxyl-protecting group include $C_{1-6}$ alkyl (e.g. methyl, ethyl, n-propyl, i-propyl, n-butyl and tert-butyl), phenyl, trityl and silyl. Examples of substituents of them include halogen atoms (e.g. fluorine, chlorine, bromine and iodine), $C_{1-6}$ alkylcarbonyl (formyl, methylcarbonyl, ethylcarbonyl and butylcarbonyl) and nitro group, and the number of the substituents ranges from about 1 to 3.

Examples of the hydroxyl-protecting group include for example, optionally substituted $C_{1-6}$ alkyl (e.g. methyl, ethyl, n-propyl, i-propyl, n-butyl and tert-butyl), phenyl, $C_{7-10}$ aralkyl (e.g. benzyl), $C_{1-6}$ alkylcarbonyl (e.g. formyl, methylcarbonyl and ethylcarbonyl), phenyloxycarbonyl, $C_{7-10}$ aralkyloxycarbonyl (e.g. benzyloxycarbonyl), pyranyl, furanyl and silyl. As the substituents mentioned above, halogen atoms (e.g. fluoro, chloro, bromo end iodo), $C_{1-6}$ alkyl, phenyl, $C_{7-10}$ aralkyl and nitro group were used. The number of substituents ranges from about 1 to 4.

And, the protecting groups can be introduced and removed by per se known means or those analogous thereto (for example, I.F.W. McOmie et al., PROTECTIVE GROUPS IN ORGANIC CHEMISTRY, Plenum Press). More specifically, those protecting groups are removed by, for example, acid, base, reduction, ultraviolet ray, hydrazine, phenylhydrazine, sodium N-methyldithiocarbamate, tetrabutyl ammonium fluoride or palladium acetate.

The compound (I) produced by the above-mentioned method can be isolated and purified by a conventional separating means such as recrystallization, distillation and chromatography. When the compound (I) thus obtained is in the free form, it can be converted to a salt by per se known means or analogous means thereto (e.g. neutralization). Conversely, when the compound (I) is obtained in the form of a salt, it can be converted to the free form or any other salt by per se known means or analogous means thereto.

Although several typical processes for the preparation of compounds (I) have been described above, compounds (I) may also be prepared according to modifications of these processes.

In the hair revitalizing tonic compositions of the present invention, any of various pharmaceutically or cosmetically acceptable vehicles and other components usable in hair revitalizing tonic compositions may also be incorporated to such an extent as to exert no adverse influence on the hair growth promotion effect of compounds (I). They comprehend active components and adjuvants which are considered to have a hair generating effect and the like in themselves. Examples thereof include plant extracts such as swertia herb extract and ginseng extract; vitamins such as vitamin $B_6$, vitamin E and derivatives thereof, and biotin; hair generating agents and hair generating aids such as pantothenic acid and derivatives thereof, glycyrrhizinic acid and derivatives thereof (e.g., monoammonium glycyrrhezinate), glycyrrhetinic acid and derivatives thereof, nicotinic acid esters (e.g., benzyl nicotinate), cyclosporins, carpronium chloride, cepharanthine, oxendolone, diazoxide, minoxidil and ethynylestradiol; antibacterial agents such as hinokitiol, hexachlorophene, phenol, isopropylmethylphenol, benzalkonium chloride, cetylpyridinium chloride, undecylenic acid, trichlorocarbanilide and bithionol; refrigerants such as menthol and eucalyptus oil; drugs such as salicylic acid, zinc and derivatives thereof, and lactic acid and alkyl esters thereof; organic acids such as citric acid, succinic acid and malic acid; amino acids such as arginine; oil components such as silicon oil, olive oil, squalane, vaseline, liquid paraffin, isopropyl myristate and isocetyl octanoate, higher fatty acids such as stearic acid and higher alcohols such as cetanol and cetostearil alcohol; polyhydric alcohols such as glycerin, propylene glycol, 1,3-butylene glycol, dipropylene glycol and polyethylene glycol; polyhydric alcohol esters such as glyceryl monostearate; surfactants such as alkyl sulfates, polyoxyethylene hydrogenated castor oils, cocoacyl N-methyl taurates, polyoxyethylene alkyl ethers, fatty acid diethanolamides, ethylene glycol fatty acid esters, alkyltrimethyl ammonium chlorides, sorbitan monooleiates and amine oxides; high molecular compounds such as carboxymethyl cellulose; sequestering agents such as hexametaphosphate and disodium edetate; perfumes; antioxidants; ultraviolet absorbers; dyes; ethanol; water; humectants; thickeners; and preservatives such as alkyl parabens. Especially, the above-mentioned antibacterail agents are preferably used in combination with compounds (I).

The hair revitalizing tonic compositions of the present invention may be prepared in any dosage form that can be applied to the integument, such as a liquid, emulsion, ointment, cream, gel or aerosol, and may be provided in various product forms such as tonics, conditioners, scalp treatments; shampoo liquids; and rinsing liquids.

In preparing these hair revitalizing tonic compositions, any of the apparatus and methods commonly used in the relevant technical field may be used to mix various ingredients and solubilize or knead the mixture.

Since the compounds of the above formula (I) have very low toxicity to human beings, hair revitalizing tonic compositions containing them according to the present invention can be percutaneously administered by applying them directly to the skin or hair or spraying them directly over the skin or hair. The dosage of these hair revitalizing tonic compositions cannot be definitely determined because it may vary with the age, individual, severity of symptoms, and the like. For human beings, however, the compounds of formula (I) are generally administered in a daily dose of 0.01 to 100 mg, preferably 0.1 to 50 mg, per kg of body weight. This dose may be administered once a day or in two to four divided doses.

The action and effects of the hair revitalizing tonic compositions of the present invention can be confirmed by evaluating the hair generating effect of each compound or composition, particularly in substantially the same manner as in the hair growth tests which will be described later, and putting it to practical use on the basis of the results thus obtained, if necessary.

Thus, the present invention provides hair revitalizing tonic compositions for mammals (including man) requiring a hair revitalization or hair loss prevention treatment and, more specifically, hair revitalizing tonic compositions which are highly effective for the promotion of hair growth, the stimulation of hair growth, the prevention of hair loss, the prevention of an itchy scalp, and the prevention of dandruff, as well as a method for applying these hair revitalizing tonic compositions to such mammals.

The present invention is more specifically explained with reference to the following synthesis example and working examples.

SYNTHESIS EXAMPLE 1

3-Hydroxy-2,2-dimethylpropyl N-octadecylcarbamate (or 2,2-dimethyl-3-(octadecylcarbamoyloxy)-1-propanol)

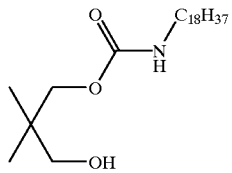

To a stirred methylene chloride solution (15 ml) containing 2.08 g (20.00 mmol) of 2,2-dimethyl-1,3-propanediol and 2.12 g (21.00 mmol) of triethylamine was added dropwise 5.91 g (20.00 mmol) of octadecyl isocyanate at room temperature, followed by stirring at room temperature for 21 hours. The reaction mixture was diluted with chloroform (15 ml) and filtered to remove any insoluble matter. The filtrate was washed with 1N hydrochloric acid, a saturated aqueous solution of sodium hydrogen carbonate, and a saturated aqueous solution of sodium chloride. After being dried over anhydrous magnesium sulfate, the filtrate was concentrated under reduced pressure. The resulting residue was separated and purified by silica gel (250 ml) column chromatography (chloroform:methanol=50:1 to 20:1) to obtain 6.56 g of the title compound (in a 82% yield).

SYNTHESIS EXAMPLE 2

2,2-Dimethyl-3-(octadecyloxy)-1-propanol

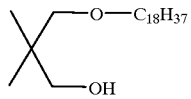

To an N,N-dimethylformamide solution (50 ml) containing 2.500 g of 2,2-dimethyl-1,3-propanediol was added an about 60% oil suspension containing 2.112 g of sodium hydride. After the reaction mixture was stirred under cooling with ice for 1 hour, 9.930 g of 1-bromo-octadecane was added dropwise thereto. After the reaction mixture was stirred at room temperature for 16.5 hours, water was added thereto and this mixture was extracted with hexane and ethyl acetate. The organic layer was washed with a saturated aqueous solution of sodium chloride, dried over anhydrous magnesium sulfate, and then concentrated under reduced pressure. The resulting residue was subjected to silica gel column chromatography (hexane:ethyl acetate=100:0 to 20:1). Thus, 4.700 g of the title compound was obtained in the form of a white solid.

$^1$H-NMR (CDCl$_3$) δ: 0.88 (3H, t, J=6.8 Hz), 0.92 (6H, s), 1.2–1.35 (30H, m), 1.56 (2H, m), 2.91 (1H, t, J=5.4 Hz), 3.27 (2H, s), 3.40 (2H, t, J=6.6 Hz), 3.45 (2H, d, J=5.4 Hz).

EXAMPLE 1

2,2-Dimethyl-3-{[(octadecylamino)carbonyl]oxy}-propyl N-[3-(dimethylamino)propyl]carbamate (or 2,2-dimethyl-3-{(3'-dimethylaminopropyl)carbamoyloxy}-1-(octadecylcarbamoyloxy)propane) (Compound 1)

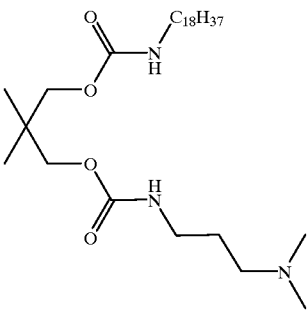

To a stirred methylene chloride solution (35 ml) containing 6.12 g (15.31 mmol) of 2,2-dimethyl-3-(octadecylcarbamoyloxy)-1-propanol and 2.42 g (30.62 mmol) of pyridine was added dropwise 2.40 g (15.31 mmol) of phenyl chlorocarbonate under cooling with ice, followed by stirring at room temperature for 1.5 hours. The reaction mixture was washed with a saturated aqueous solution of sodium hydrogen carbonate, dried over anhydrous magnesium sulfate, and then concentrated under reduced pressure. To the resulting residue was added 1.56 g (15.31 mmol) of N,N-dimethyl-1,3-propanediamine, followed by stirring at 70° C. for 5 hours. The reaction mixture was separated and purified by silica gel (200 ml) column chromatography (chloroform:methanol=100:1 to 10:1) to obtain 7.57 g of the title compound (in a 94% yield). 470 mg of this compound was dissolved in a solvent mixture composed of 0.5 ml of acetone and 3 ml of hexane by the application of heat, and recrystallized by allowing the resulting solution to stand at 0° C. for 6 hours. Thus, there was obtained 220 mg of a purified product (with a purity of 98.4% as expressed in terms of an HPLC area percentage).

Melting point: 53.2–53.8° C. $^1$H-NMR (CDCl$_3$) δ: 0.88 (3H, t, J=6.8 Hz), 0.93 (6H, s), 1.25 (30H, m), 1.48 (2H, m), 1.66 (2H, m), 2.23 (6H, s), 2.35 (2H, t, J=6.8 Hz), 3.15 (2H, m), 3.24 (2H, dt, J=6.1, 6.3 Hz), 3.86 (4H, m), 4.69 (1H, brs), 5.49 (1H, brs).

EXAMPLE 2

2,2-Dimethyl-3-{[(octadecylamino)carbonyl]oxy}-propyl N-[3-(dimethylamino)propyl]carbamate hydrochloride (Compound 2)

To a stirred ethyl acetate solution (40 ml) containing 5.96 g (11.29 mmol) of 2,2-dimethyl-3-{(3'-dimethylaminopropyl)-carbamoyloxy}-1-(octadecylcarbamoyloxy)propane was added dropwise 2.96 ml (11.86 mmol) of a 4N hydrogen chloride solution in ethyl acetate under cooling with ice, followed by stirring for 0.5 hour under cooling with ice. The resulting precipitate was separated by filtration and washed with ethyl acetate to obtain 6.05 g of the title compound (in a 95% yield). Recrystallization of this compound from a solvent mixture composed of ethanol and ethyl acetate was repeated four times to obtain 2.51 g of a purified product (with a purity of 99.0% as expressed in terms of an HPLC area percentage).

Melting point: 83.0–84.0° C. $^1$H-NMR (CDCl$_3$) δ: 0.88 (3H, t, J=6.9 Hz), 0.94 (6H, s), 1.25 (30H, m), 1.49 (2H, m), 2.09 (2H, dt, J=6.5, 7.0 Hz), 2.81 (3H, s), 2.82 (3H, s), 3.10–3.17 (4H, m), 3.37 (2H, dt, J=5.9, 6.1 Hz), 3.86 (4H, m), 4.81 (1H, brs), 5.72 (1H, brs).

EXAMPLE 3

2,2-Dimethyl-3-{[(octadecylamino)carbonyl]oxy}-porpyl N-[(2-piperidinoethyl)carbamate (Compound 3)

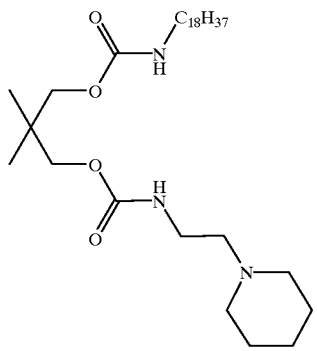

To a methylene chloride solution (5 ml) containing 500 mg of 2,2-dimethyl-3-octadecylcarbamoyloxy-1-propanol (or 3-hydroxy-2,2-dimethylpropyl N-octadecylcarbamate) were added 198 mg of pyridine and 215 mg of phenyl chlorocarbonate under cooling with ice, followed by stirring at room temperature for 1.5 hours. The reaction mixture was washed with a saturated aqueous solution of sodium hydrogen carbonate, dried over anhydrous magnesium sulfate, and then concentrated under reduced pressure. To the resulting residue was added 192 mg of 1-(2-aminoethyl)piperidine, followed by stirring at 70° C. for 5 hours. The reaction mixture was subjected to silica gel column chromatography (chloroform:methanol=100:0 to 98:2). Thus, 670 mg of the title compound was obtained in the form of a white solid.

$^1$H-NMR (CDCl$_3$) δ: 0.88 (3H, t, J=6.8 Hz), 0.94 (6H, s), 1.2–1.35 (30H, m), 1.4–1.5 (4H, m), 1.57 (4H, m), 2.37 (4H, m), 2.42 (2H, t, J=6.1 Hz), 3.15 (2H, m), 3.26 (2H, m), 3.87 (4H, s), 4.72 (1H, brt), 5.20 (1H, brt).

EXAMPLE 4

2,2-Dimethyl-3-{[[(3-morpholinopropyl)amino]-carbonyl]oxy]propyl N-octadecylcarbamate (Compound 4)

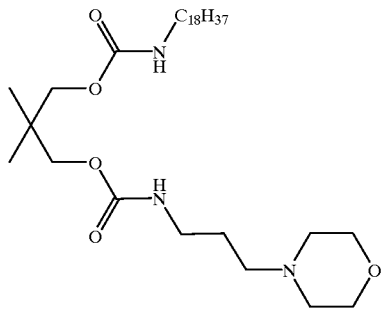

To a methylene chloride solution (3 ml) containing 500 mg of 2,2-dimethyl-3-octadecylcarbamoyloxy-1-propanol (or 3-hydroxy-2,2-dimethylpropyl N-octadecylcarbamate) were added 198 mg of pyridine and 215 mg of phenyl chlorocarbonate under cooling with ice, followed by stirring at room temperature for 1.5 hours. The reaction mixture was washed with a saturated aqueous solution of sodium hydrogen carbonate, dried over anhydrous magnesium sulfate, and then concentrated under reduced pressure. To the resulting residue was added 216 mg of 4-(3-aminopropyl)morpholine, followed by stirring at 70° C. for 5 hours. The reaction mixture was subjected to silica gel column chromatography (chloroform:methanol=100:0 to 98:2). Thus, 766 mg of the title compound was obtained in the form of a white solid.

$^1$H-NMR (CDCl$_3$) δ: 0.88 (3H, t, J=6.8 Hz), 0.94 (6H, s), 1.2–1.35 (30H, m), 1.48 (2H, m), 1.67 (2H, quintet, J=6.4 Hz), 2.41–2.49 (6H, m), 3.15 (2H, q, J=6.6 Hz), 3.26 (2H, q, J=6.4 Hz), 3.71 (4H, t, J=4. 6 Hz), 3.85 (4H, s), 4.72 (1H, brt), 5.78 (1H, brt).

EXAMPLE 5

2,2-Dimethyl-3-{[[(3-morrholinorroryl)amino]-carbonyl]oxy]propyl N-octadecylcarbamate hydrochloride (Compound 5)

To an ethyl acetate solution (37 ml) containing 3.650 g of 2,2-dimethyl-3-{[[(3-morpholinopropyl)-amino]carbonyl]oxy]propyl N-octadecylcarbamate was added 1.8 ml of a 4N hydrogen chloride solution in ethyl acetate under cooling with ice, followed by stirring for 0.5 hour. After the reaction mixture was concentrated under reduced pressure, the resulting residue was recrystallized from a mixture of ethanol and ethyl acetate to obtain 3.671 g of the title compound in the form of a white solid.

$^1$H-NMR (CDCl$_3$) δ: 0.88 (3H, t, J=6.8 Hz), 0.94 (6H, s), 1.2–1.35 (30H, m), 1.49 (2H, m), 2.14 (2H, quintet, J=6.4 Hz), 2.88 (2H, m), 3.09 (2H, m), 3.14 (2H, q, J=6.8 Hz), 3.36 (2H, q, J=6.4 Hz), 3.46 (2H, d, J=11.7 Hz), 3.86 (4H, s), 3.98 (2H, dd, J=1 2.9, 3.2 Hz), 4.31 (2H, t, J=11.7 Hz), 4.80 (1H, brt), 5.74 (1H, brt), 12.75 (1H, brs).

EXAMPLE 6

2,2-Dimethyl-3-{[(octadecylamino)carbonyl]oxy}-propyl N-[3-(diethylamino)prolyl]carbamate (Compound 6)

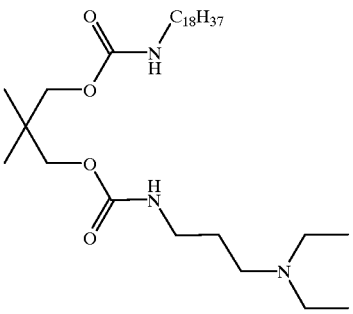

To a methylene chloride solution (3 ml) containing 500 mg of 2,2-dimethyl-3-octadecylcarbamoyloxy-1-propanol (or 3-hydroxy-2,2-dimethylpropyl N-octadecylcarbamate) were added 198 mg of pyridine and 215 mg of phenyl chlorocarbonate under cooling with ice, followed by stirring at room temperature for 1.5 hours. The reaction mixture was washed with a saturated aqueous solution of sodium hydrogen carbonate, dried over anhydrous magnesium sulfate, and then concentrated under reduced pressure. To the resulting residue was added 195 mg of 3-diethylaminopropylamine, followed by stirring at 70° C. for 5 hours. The reaction mixture was subjected to silica gel column chromatography (chloroform:methanol=99:1 to 93:7). Thus, 615 mg of the title compound was obtained in the form of a white solid.

$^1$H-NMR (CDCl$_3$) δ: 0.88 (3H, t, J=6.8 Hz), 0.94 (6H, s), 1.05 (6H, t, J=7.1 Hz), 1.2–1.35 (30H, m), 1.49 (2H, m), 1.66 (2H, quintet, J=6.4 Hz), 2.53 (2H, t, J=6.4 Hz), 2.54 (4H, q, J=7.1 Hz), 3.15 (2H, q, J=6.6 Hz), 3.25 (2H, q, J=6.4 Hz), 3.86 (4H, s), 4.66 (1H, brt), 6.02 (1H, brt).

EXAMPLE 7

2,2-Dimethyl-3-{[(octadecylamino)carbonyl]oxy}-propyl 4-methyltetrahydro-1(2H)-pyrazinecarboxylate (Compound 7)

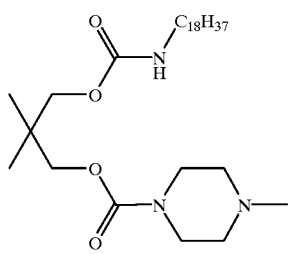

To a methylene chloride solution (23 ml) containing 2.30 g of 2,2-dimethyl-3-octadecylcarbamoyloxy-1-propanol (or 3-hydroxy-2,2-dimethylpropyl N-octadecylcarbamate) were added 0.68 g of pyridine and 1.00 g of phenyl chlorocarbonate under cooling with ice, followed by stirring at room temperature for 3 hours. The reaction mixture was diluted with chloroform, washed successively with 1N hydrochloric acid, a saturated aqueous solution of sodium hydrogen carbonate, and a saturated aqueous solution of sodium chloride, dried over anhydrous magnesium sulfate, and then concentrated under reduced pressure. To the resulting residue was added 0.64 g of N-methylpiperazine, followed by stirring at 70° C. for 3 hours. The reaction mixture was subjected to silica gel column chromatography (ethyl acetate: methanol=30:1 to 10:1). Thus, 2.77 g of the title compound was obtained in the form of a white solid.

$^1$H-NMR (CDCl$_3$) δ: 0.88 (3H, t, J=6.8 Hz), 0.95 (6H, s), 1.2–1.35 (30H, m), 1.48 (2H, m), 2.30 (3H, s), 2.36 (4H, t, J=4.9 Hz), 3.16 (2H, q, J=6.8 Hz), 3.49 (4H, t, J=4.9 Hz), 3.87 (2H, s), 3.89 (2H, s), 4.66 (1H, brt).

EXAMPLE 8

2,2-Dimethyl-3-{[(octadecylamino)carbonyl]oxy}-propyl 4-methyltetrahydro-1(2H)-pyrazinecarboxylate hydrochloride (Compound 8)

To an ethyl acetate solution (25 ml) containing 2.500 g of 2,2-dimethyl-3-{[(octadecylamino)carbonyl]oxy}propyl 4-methyltetrahydro-1(2H)-pyrazinecarboxylate was added 1.42 ml of a 4N hydrogen chloride solution in ethyl acetate, followed by stirring at room temperature for 0.5 hour. After the reaction mixture was concentrated under reduced pressure, the resulting residue was recrystallized from a mixture of ethanol and ethyl acetate to obtain 2.323 g of the title compound in the form of a white solid.

$^1$H-NMR (CDCl$_3$) δ: 0.88 (3H, t, J=6.8 Hz), 0.96 (6H, s), 1.2–1.35 (30H, m), 1.49 (2H, m), 2.81 (3H, d, J=2.4 Hz), 2.92 (2H, m), 3.13 (2H, q, J=6.4 Hz), 3.41 (2H, d, J=11.7 Hz), 3.74 (4H, m), 4.05 (2H, m), 4.19 (2H, m), 4.69 (1H, brt), 13.21 (1H, brt).

EXAMPLE 9

2,2-Dimethyl-3-(octadecyloxy)propyl N-[3-(dimethylamino)propyl]carbamate (Compound 9)

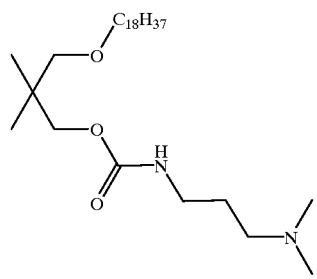

To a methylene chloride solution (36 ml) containing 3.567 g of 2,2-dimethyl-3-(octadecyloxy)-1-propanol were added 1.187 g of pyridine and 1.723 g of phenyl chlorocarbonate under cooling with ice, followed by stirring at room temperature for 2 hours. The reaction mixture was diluted with chloroform, washed successively with 1N hydrochloric acid, a saturated aqueous solution of sodium hydrogen carbonate, and a saturated aqueous solution of sodium chloride, dried over anhydrous magnesium sulfate, and then concentrated under reduced pressure. To half (2.384 g) of the resulting white solid was added 0.763 g of N,N-dimethyl-1,3-propanediamine, followed by stirring at 70° C. for 1.5 hours. The reaction mixture was subjected to silica gel column chromatography (chloroform:methanol=30:1). Thus, 1.939 g of the title compound was obtained in the form of a white solid.

$^1$H-NMR (CDCl$_3$) δ: 0.88 (3H, t, J=6.8 Hz), 0.91 (6H, s), 1.2–1.35 (30H, m), 1.53 (2H, m), 1.66 (2H, quintet, J=6.8 Hz), 2.21 (6H, s), 2.33 (2H, t, J=6.8 Hz), 3.14 (2H, s), 3.24 (2H, m), 3.37 (2H, t, J=6.6 Hz), 3.87 (2H, s), 5.40 (1H, brt).

EXAMPLE 10

2,2-Dimethyl-3-(octadecyloxy)porpyl N-[3-(dimethylamino)propyl]carbamate hydrochloride (Compound 10)

To an ethyl acetate solution (15 ml) containing 1.454 g of 2,2-dimethyl-3-(octadecyloxy)propyl N-[3-(dimethylamino)propyl]carbamate was added 0.75 ml of a 4N hydrogen chloride solution in ethyl acetate, followed by stirring at room temperature for 10 minutes. After the reaction mixture was concentrated under reduced pressure, the resulting residue was recrystallized from a mixture of ethanol and ethyl acetate to obtain 1.117 g of the title compound in the form of a white solid.

$^1$H-NMR$^1$ (CDCl$_3$) δ: 0.88 (3H, t, J=7.1 Hz), 0.91 (6H, s), 1.2–1.35 (30H, m), 1.53 (2H, m), 2.07 (2H, m), 2.80 (6H, s), 3.08 (2H, t, J=7.1 Hz), 3.14 (2H, s), 3.35 (2H, m), 3.37 (2H, t, J=6.4 Hz), 3.87 (2H, s), 5.68 (1H, brt).

EXAMPLE 11

2,2-Dimethyl-3-(octadecyloxy)porpyl N-(3-morphoinopropyl)carbamate (Compound 11)

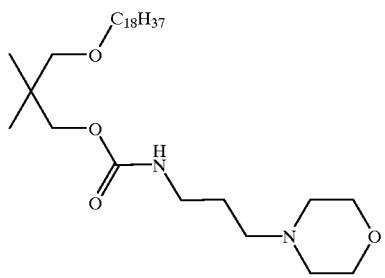

To half (2.384 g) of the intermediate obtained in Example 9 in the form of a while solid was added 0.832 g of 4-(3-aminopropyl)morpholine, followed by stirring at 70° C. for 1.5 hours. The reaction mixture was subjected to silica gel column chromatography (chloroform:methanol=100:0 to 20:1). Thus, 2.597 g of the title compound was obtained in the form of a white solid.

$^1$H-NMR (CDCl$_3$) δ: 0.88 (3H, t, J=6.8 Hz), 0.91 (6H, s), 1.2–1.35 (30H, m), 1.53 (2H, m), 1.68 (2H, quintet, J=6.8 Hz), 2.44 (6H, m), 3.14 (2H, s), 3.27 (2H, m), 3.37 (2H, t, J=6.6 Hz), 3.71 (4H, t, J=4.6 Hz), 3.87 (2H, s), 5.77 (1H, brt).

EXAMPLE 12

2,2-Dimethyl-3-(octadecyloxy)prolyl N-(3-morpholinopropyl)carbamate hydrochloride (Compound 12)

To an ethyl acetate solution (16 ml) containing 1.581 g of 2,2-dimethyl-3-(octadecyloxy)propyl N-(3-morpholinopropyl)carbamate was added 0.75 ml of a 4N hydrogen chloride solution in ethyl acetate, followed by stirring at room temperature for 15 minutes. After the reaction mixture was concentrated under reduced pressure, the resulting residue was recrystallized from a mixture of ethanol and ethyl acetate to obtain 1.218 g of the title compound in the form of a white solid.

$^1$H-NMR (CDCl$_3$) δ: 0.88 (3H, t, J=7.3 Hz), 0.91 (6H, s), 1.2–1.35 (30H, m), 1.53 (2H, m), 2.09 (2H, m), 2.95–3.15 (6H, m), 3.14 (2H, s), 3.35 (2H, m), 3.37 (2H, t, J=6.6 Hz), 3.86 (2H, s), 4.08 (4H, m), 5.70 (1H, brt).

Evaluation Method (hair growth test procedure)

Hair revitalizing tonic compositions in accordance with the present invention, which will be described later, can be evaluated according to the following hair growth test procedure.

Using C3H/HeNCrJ mice which are in the resting stage of a hair cycle, hair growth tests on samples are carried out according to the method of Ogawa et al. [M. Seiji and I. A. Bernstein (ed.), "Normal and Abnormal Epidermal Differentiation" (Todai Shuppan, 1982), pp. 159–170].

Specifically, mice are shaved in the back with a hair clipper and a shaver, and used in groups of ten. In test groups, 0.1 ml of each sample is applied to the mice once a day, while no sample is applied in a control group. The hair generating effects of the samples are evaluated by measuring the area of a hair generating part in the back of the mouse and expressing it as a percentage.

(a) The number of days required for 50% hair growth is recorded, and the data obtained with the samples are compared with those obtained with controls and, if necessary, a comparative composition. Measurements are made on the 18th, 24th, 30th, 37th and 43rd days.

(b) Alternatively, the area of a hair generating part was measured on the 24th day after application of the sample.

EXAMPLE 13

(hair growth tests)

Using the following Compositions 1 and 2, hair growth tests were carried out according to the above-described procedure (a).

The results thus obtained are shown in Table 1.

Preparation of Composition 1

0.1 g of compound 1, 70.0 g of 95% ethanol and 29.9 g of ion-exchanged water were mixed, and this mixture was stirred to obtain a solution composition.

Preparation of Composition 2

0.1 g of compound 2, 70.0 g of 95% ethanol and 29.9 g of ion-exchanged water were mixed, and this mixture was stirred to obtain a solution composition.

Preparation of Comparative Composition 0.1 g of croton oil, 70.0 g of 95% ethanol and 29.9 g of ion-exchanged water were mixed, and this mixture was stirred to obtain a solution composition.

A composition to which neither compound nor croton oil was added was used as Control 2.

TABLE 1

| | Composition 1 | Composition 2 | Comparative Composition (croton oil) | Control 1 (no application) | Control 2 (no addition) |
|---|---|---|---|---|---|
| Number of days required for 50% hair growth | 18 days or less | 18 days or less | 19 to 37 days | 150 days or more | 19 to 37 days |

EXAMPLE 14

(hair growth tests)

Using the following Compositions 3 to 6, hair growth tests were carried out according to the abovedescribed procedure (b).

The results thus obtained are shown in Table 2.

Preparation of Compositions 3 to 6

0.2 g each of Compound 5, Compound 8, Compound 10 and Compound 12 were separately mixed with 70.0 g of 95% ethanol and 29.8 g of ion-exchanged water. These mixtures were stirred to obtain Compositions 3 to 6 in the form of homogeneous solutions.

TABLE 2

| Composition No. (Compound No. used) | Degree of hair generation (%) |
|---|---|
| 3 (Compound 5) | 100 |
| 4 (Compound 8) | 100 |
| 5 (Compound 10) | 100 |
| 6 (Compound 12) | 100 |

EXAMPLE 15

(preparation examples)

Preparation Example 1

A lotion haylng the following composition was prepared.

|  | (wt. %) |
|---|---|
| 95% ethanol | 50.0 |
| Monoammonium glycyrrhizinate | 0.1 |
| Compound 1 | 1.0 |
| Sodium lauryl sulfate | 0.1 |
| Hydrogenated castor oil ethylene oxide (40 mole) adduct | 0.5 |
| Succinic acid | q. s. |
| Perfume and dye | q. s. |
| Purified water | Balance |

<Preparation method>

Hydrogenated castor oil ethylene oxide (40 mole) adduct and a perfume were dissolved in 95% ethanol, followed by the addition of purified water. Then, other ingredients were added thereto and dissolved therein with stirring to obtain a clear liquid lotion.

Preparation Example 2

A lotion haylng the following composition was prepared.

|  | (wt. %) |
|---|---|
| 95% ethanol | 50.0 |
| Vitamin E acetate | 0.05 |
| Compound 2 | 0.01 |
| Sodium lauryl sulfate | 0.06 |
| Propylene glycol | 0.1 |
| Hydrogenated castor oil ethylene oxide (40 mole) adduct | 0.5 |
| Lactic acid | q. s. |
| Sodium lactate | q. s. |
| Perfume and dye | q. s. |
| Purified water | Balance |

<Preparation method>

Hydrogenated castor oil ethylene oxide (40 mole) adduct and a perfume were dissolved in 95% ethanol, followed by the addition of purified water. Then, other ingredients were added thereto and dissolved therein with stirring to obtain a clear liquid lotion.

The hair revitalizing tonic compositions obtained in Preparation Examples 1 and 2 had an excellent hair loss prevention and hair revitalizing effect and, moreover, an excellent dandruff and itchy scalp prevention effect.

Preparation Example 3

A hair tonic haylng the following composition was prepared.

|  | (wt. %) |
|---|---|
| Compound 2 | 0.1 |
| Hinokitiol | 1.0 |
| Vitamin $B_6$ | 0.2 |
| Vitamin F acetate | 0.02 |
| Menthol | 0.2 |
| Swertia herb extract | 1.0 |
| Salicylic acid | 0.1 |
| Propytene glycol | 2.0 |
| Polyoxyethylene (10 mole) monostearate | 2.0 |
| 75% ethanol | Balance |

<Preparation method>

Various ingredients were successively added to 75% ethanol and dissolved therein with stirring to obtain a hair tonic.

Preparation Example 4

A hair tonic haylng the following composition was prepared.

|  | (wt. %) |
|---|---|
| Compound 1 | 0.5 |
| Compound 2 | 0.1 |
| Hinokitiol | 1.0 |
| Vitamin $B_6$ | 0.2 |
| Vitamin E | 0.02 |
| Menthol | 0.2 |
| Salicylic acid | 0.1 |
| Propylene glycol | 2.0 |
| Sodium hyatulonate | 0.01 |
| Polyoxyethylene (10 mole) monostearate | 2.0 |
| 70% ethanol | Balance |

<Preparation method>

Various ingredients were successively added to 70% ethanol and dissolved therein with stirring to obtain a hair tonic.

Preparation Example 5

An O/W emulsion haylng the following composition was prepared.

|  | (wt. %) |
|---|---|
| (Phase A) | |
| Hydrogenated castor oil polyoxyethylene (60 mole) adduct | 2.0 |
| Glycerin | 10.0 |
| Dipropylene glycol | 10.0 |
| 1,3-Butylene glycol | 4.0 |
| Compound 2 | 0.1 |
| Polyethylene glycol 1500 | 5.0 |
| (Phase B) | |
| Isocetyl octanoate | 10.0 |
| Squalane | 5.0 |
| Vaseline | 2.0 |
| Propylparaben | 2.0 |
| (Phase C) | |
| 1% aqueous solution of carboxyvinyl polymer | 30.0 |
| Sodium hexametaphosphate | 0.03 |
| Ion-exchanged water | 8.35 |

|  | (wt. %) |
|---|---|
| (Phase D) | |
| Ion-exchanged water | 4.5 |
| (Phase E) | |
| KOH | 0.12 |
| Ion-exchanged water | Balance |
| <Preparation method> | |

Phases A and B were separately dissolved by heating at 60° C., and mixed with a homomixer to obtain a gel. Then, phase D was slowly added to this gel and dispersed therein with a homomixer.

Thereafter, previously dissolved phase C was added to the above gel dispersion, and previously dissolved phase E was added thereto. This mixture was emulsified with a homomixer to obtain an O/W emulsion.

Preparation Example 6

A cream haylng the following composition was prepared.

|  | (wt. %) |
|---|---|
| (Phase A) | |
| Dimethylhexylpolyoxyethylene (5 mole) amine oxide | 2.5 |
| Liquid paraffin | 5.0 |
| Cetostearyl alcohol | 5.5 |
| Glyceryl monostearate | 3.0 |
| EO (20 mole) 2-octyldodecyl ether | 3.0 |
| Propylparaben | 0.3 |
| Perfume | 0.1 |
| (Phase B) | |
| Compound 2 | 1.0 |
| Glycerin | 8.0 |
| Dipropylene glycol | 20.0 |
| Polyethylene glycol 4000 | 5.0 |
| Sodium hexametaphosphate | 0.005 |
| Ion-exchanged water | Balance |
| <Preparation method> | |

Phases A and B were separately dissolved by heating, mixed together, and then emulsified with a homomixer to obtain a cream.

Preparation Example 7

An aerosol spray haylng the following composition was prepared.

|  | (wt. %) |
|---|---|
| (Formulation for medicinal solution) | |
| 95% ethanol | 50.0 |
| Glycyrrhetic acid | 0.1 |
| Compound 1 | 0.5 |
| Swertia herb extract | 0.1 |
| Sodium lauryl sulfate | 0.1 |
| Hydrogenated castor oil ethylene oxide (40 mole) adduct | 0.5 |
| Lactic acid | q. s. |
| Sodium lactate | q. s. |
| Perfume | q. s. |
| Ion-exchanged water | Balance |
| (Formulation for packing) | |
| Medicinal solution | 50.0 |
| Liquefied petroleum gas | 50.0 |
| <Preparation method> | |

A medicinal solution was prepared according to the formulation therefor, and packed into a container. After a valve was mounted, a gas was filled to make an aerosol spray.

Preparation Example 8

A shampoo haylng the following composition was prepared.

|  | (wt. %) |
|---|---|
| (1) Cocoylmethyltaurine sodium | 2.0 |
| (2) Polyoxyethylene (8 mole) oleyl alcohol ether | 2.0 |
| (3) Lauric acid diethanolamide | 4.0 |
| (4) Ethylene glycol fatty acid ester | 1.0 |
| (5) Glycerin | 0.2 |
| (6) Menthol | 0.1 |
| (7) Compound 2 | 0.1 |
| (8) Disodium edetate | 0.1 |
| (9) Perfume | q. s. |
| (10) Purified water | Balance |
| <Preparation method> | |

After purified water was heated to 70, ingredients (1)–(9) were successively added thereto and dissolved therein with stirring, and then cooled to obtain a shampoo.

Preparation Example 9

A rinse haylng the following composition was prepared.

|  | (wt. %) |
|---|---|
| (1) Stearyltrimethylammonium chloride | 1.5 |
| (2) Dimethylpolysiloxane (20 cs) | 3.0 |
| (3) Polyoxyethylene (10 mole) oleyl alcohol ether | 1.0 |
| (4) Glycerin | 5.0 |
| (5) Compound 1 | 0.5 |
| (6) Preservative | q. s. |
| (7) 4-tert-butyl-4'-methoxybenzoylmethane | q. s. |
| (8) Purified water | Balance |
| <Preparation method> | |

Ingredients (1), (3) and (4) were added to purified water, and this mixture was heated at 70° C. to obtain an aqueous phase. The other ingredients were melted by heating at 70° C. to obtain an oily phase. The oily phase was added to the aqueous phase, mixed there- with by means of an emulsifier, and then cooled to obtain a rinse.

Preparation Example 10

A scalp treatment having the following composition was prepared.

|  |  | (wt. %) |
|---|---|---|
| (Formulation for medicinal solution) | | |
| (1) | Liquid paraffin | 27.0 |
| (2) | Stearic acid | 5.0 |
| (3) | Cetanol | 5.0 |
| (4) | Sorbitan mono-oleate | 2.0 |
| (5) | Polyoxyethylene sorbitan mono-oleate | 3.0 |
| (6) | Compound 2 | 0.1 |
| (7) | 1,3-Butylene glycol | 5.0 |
| (8) | Preservative | q. s. |
| (9) | Purified water | Balance |
| (Formulation for packing) | | |
| Medicinal solution | | 50.0 |
| Liquefied petroleum gas | | 50.0 |

Ingredients (5) and (6) were dissolved in ingredients (1)–(4), and this mixture was heated at 80° C. until a homogeneous solution was obtained. The resulting solution was cooled to 30° C. and mixed with ingredients (7)–(9) to prepare a medicinal solution. The medicinal solution so prepared, together with a propellant, was packed into a container to make a scalp treatment.

Preparation Example 11

A scalp treatment having the following composition was prepared.

|  |  | (wt. %) |
|---|---|---|
| (1) | Hinokitiol | 0.1 |
| (2) | Swertia herb extract | 1.0 |
| (3) | Vitamin $B_6$ | 0.1 |
| (4) | Vitamin E | 0.01 |
| (5) | Menthol | 0.1 |
| (6) | Salicylic acid | 0.001 |
| (7) | Compound 1 | 0.1 |
| (8) | Polyoxyethylene sorbitan mono-oleate | 0.1 |
| (9) | Propylene glycol | 2.0 |
| (10) | 75% ethanol | Balance |
| (Formulation for packing) | | |
| Medicinal solution | | 50.0 |
| Dimethyl ether | | 50.0 |
| <Preparation method> | | |

A scalp treatment was made in the same manner as preparation example 10.

What is claimed is:

1. A tonic composition for the promotion or stimulation of hair growth comprising a compound of the following formula (I), or a salt thereof, in an amount effective for the promotion or stimulation of hair growth in a mammal, together with a pharmaceutically or cosmetically acceptable vehicle or other component useable in a hair tonic composition:

Formula (I):

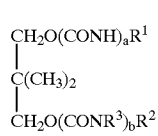

wherein
$R^1$ and $R^2$ are each independently:
1) a $C_{1-30}$ hydrocarbon group which is optionally substituted, said $C_{1-30}$ hydrocarbon group is selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups, wherein when the $C_{1-30}$ hydrocarbon group is substituted, the substituents are one to five substituents selected from the group consisting of halogen, hydroxyl, mercapto, oxo, thioxo, cyano, carbamoyl, carboxyl, $C_{1-4}$ alkoxycarbonyl, sulfo, $C_{1-4}$ alkoxy, phenoxy, halogenophenoxy, $C_{1-4}$ alkylthio, phenylthio, $C_{1-4}$ alkylsulfinyl, $C_{1-10}$ haloalkyl, amino, $C_{1-6}$ acylamino, $C_{1-30}$ alkylamino, di-$C_{1-4}$ alkylamino, $C_{1-5}$ acyl, benzoyl, and five- or six-membered heterocyclic groups which contain 1 to 4 heteroatoms selected from oxygen, sulfur or nitrogen atoms and which are optionally substituted by 1 to 4 substituents selected from the group consisting of a halogen atom and a $C_{1-4}$ alkyl group; or
2) a five- or six-membered heterocyclic group which contains 1 to 4 heteroatoms selected from oxygen, sulfur or nitrogen atoms and which is optionally substituted with a substituent selected from the group consisting of a halogen atom and a $C_{1-4}$ alkyl group;

$R^3$ is
1) a hydrogen atom;
2) an alkyl group which is optionally substituted with $C_{1-5}$ alkoxycarbonyl;
3) an acyl group;
4) an alkoxycarbonyl group;
5) a phenoxycarbonyl group; or
6) a carbamoyl group which is optionally substituted with a substituent selected from the group consisting of $C_{1-5}$ alkyl, di-$C_{1-5}$ alkyl, and three- or seven-membered cyclic groups; and a and b are each independently 0 or 1.

2. The tonic composition for the promotion or stimulation of hair growth as claimed in claim 1, wherein $R^1$ is a $C_{1-30}$ hydrocarbon group selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups.

3. The tonic composition for the promotion or stimulation of hair growth as claimed in claim 1, wherein $R^2$ is a $C_{1-30}$ hydrocarbon group substituted by amino, $C_{1-6}$ acylamino, $C_{1-30}$ alkylamino, di-$C_{1-4}$ alkylamino, or five- or six-membered heterocyclic groups which contain 1 to 4 heteroatoms selected from oxygen, sulfur or nitrogen atoms and which is optionally substituted by 1 to 4 substituents selected from the group consisting of a halogen atom and a $C_{1-4}$ alkyl group, wherein said $C_{1-30}$ hydrocarbon group is selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups.

4. The tonic composition for the promotion or stimulation of hair growth as claimed in claim 1, wherein $R^1$ is a $C_{1-30}$ hydrocarbon group selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups, and $R^2$ is a $C_{1-30}$ hydrocarbon group substituted by amino, $C_{1-6}$ acylamino, $C_{1-30}$ alkylamino, di-$C_{1-4}$ alkylamino, or five- or six-membered heterocyclic groups which contain 1 to 4 heteroatoms selected from oxygen, sulfur or nitrogen atoms and which is optionally substituted by 1 to 4 substituents selected from the group consisting of a halogen atom and a $C_{1-4}$ alkyl group, wherein the $C_{1-30}$ hydrocarbon group for $R^2$ is selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ arlkyl groups.

5. The tonic composition for the promotion or stimulation of hair growth as claimed in claim 1, wherein $R^2$ is a group of the formula $$-(CH_2)_n \underset{R^5}{\overset{}{N}}-R^4$$

wherein $R^4$ and $R^5$ are each independently a hydrogen atom or a $C_{1-5}$ alkyl group which is optionally substituted by hydroxyl, and n is an integer of 1 to 10.

6. The tonic composition for the promotion or stimulation of hair growth as claimed in claim 1, wherein $R^2$ is a group of the formula $$-(CH_2)_n \underset{R^5}{\overset{}{N}}-R^4$$

wherein $R^4$ and $R^5$ are each independently a hydrogen atom or a $C_{1-5}$ alkyl group which is optionally substituted by hydroxyl, n is an integer of 1 to 10, and $R^1$ is a $C_{1-30}$ hydrocarbon group selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups.

7. The tonic composition for the stimulation or promotion of hair growth as claimed in claim 1, wherein $R^2$ is a group of the formula $$-(CH_2)_n \underset{R^5}{\overset{}{N}}-R^4$$

wherein $R^4$ and $R^5$ are each independently a $C_{1-3}$ alkyl group and n is an integer of 1 to 10.

8. The tonic composition for the stimulation or promotion of hair growth as claimed in claim 1, wherein $R^2$ is a group of the formula $$-(CH_2)_n \underset{R^5}{\overset{}{N}}-R^4$$

wherein $R^4$ and $R^5$ form a five- or six-membered nitrogen-containing heterocyclic ring in conjunction with the adjacent nitrogen atom, and n is an integer of 1 to 10.

9. The tonic composition for the stimulation or promotion of hair growth as claimed in claim 1, wherein $R^2$ is a group of the formula $$-(CH_2)_n \underset{R^5}{\overset{}{N}}-R^4$$

wherein $R^4$ and $R^5$ form a five- or six-membered heterocyclic ring through the adjacent nitrogen atom, said heterocyclic ring containing a heteroatom selected from a group consisting of oxygen, nitrogen and sulfur atoms in addition to said adjacent nitrogen atom.

10. The tonic composition for the stimulation or promotion of hair growth as claimed in claim 1, wherein $R^2$ is a group of the formula $$-(CH_2)_n \underset{R^5}{\overset{}{N}}-R^4$$

wherein $R^4$ and $R^5$ is combined with $R^3$ to form alkylene or alkenylene bridge which may optionally contain one or more oxo groups, the other of $R^4$ and $R^5$ is $C_{1-3}$ alkyl group, and n is an integer of 1 to 10.

11. The tonic composition for the stimulation or promotion of hair growth as claimed in claim 10, wherein $R^3$ and the adjacent nitrogen are combined with $R^2$ to form a group of the formula $$-N\underset{}{\diagup\!\!\diagdown}N-CH_3 \quad \text{or} \quad -N\underset{O}{\diagup\!\!\diagdown}N-CH_3.$$

12. The tonic composition for the promotion or stimulation of hair growth as claimed in claim 1, wherein the compound of formula (1) is a compound selected from the group consisting of:

2,2-dimethyl-3-{[(octadecylamino)carbonyl]-oxy}propyl N-[3-(dimethylamino)propyl]carbamate or a salt thereof;

2,2-dimethyl-3-{[(octadecylamino)carbonyl]-oxy}propyl N-[(2-piperidinoethyl)carbamate or a salt thereof;

2,2-dimethyl-3-{[[(3-morpholinopropyl)amino]-carbonyl]oxy]propyl N-octadecylcarbamate or a salt thereof;

2,2-dimethyl-3-{[(octadecylamino)carbonyl]-oxy}propyl N-[3-(diethylamino)propyl]carbamate or a salt thereof;

2,2-dimethyl-3-{[(octadecylamino)carbonyl]-oxy}propyl 4-methyltetrahydro-1(2H)-pyrazinecarboxylate or a salt thereof;

2,2-dimethyl-3-(octadecyloxy)propyl N-[3-(dimethylamino)propyl]carbamate or a salt thereof; and 2,2-dimthyl-3-(octadecyloxy)propyl N-(3-morpholinopropyl)carbamate or a salt thereof.

13. A topical hair promoting or stimulating tonic comprising the composition of claim 1.

14. A hair promoting or stimulating method for a mammal which comprises topically applying an effective amount for the promotion or stimulation of hair growth of a compound of the following formula (I), or a pharmaceutically or cosmetically acceptable salt thereof, to the skin or hair of a mammal requiring a hair promoting or stimulating treatment:

Formula (I):

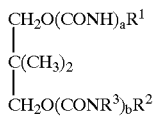

wherein
- $R^1$ and $R^2$ are each independently:
  1) a $C_{1-30}$ hydrocarbon group which is optionally substituted, said $C_{1-30}$ hydrocarbon group is selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups, wherein when the $C_{1-30}$ hydrocarbon group is substituted, the substituents are one to five substituents selected from the group consisting of halogen, hydroxyl, mercapto, oxo, thioxo, cyano, carbamoyl, carboxyl, $C_{1-4}$ alkoxycarbonyl, sulfo, $C_{1-4}$ alkoxy, phenoxy, halogenophenoxy, $C_{1-4}$ alkylthio, phenylthio, $C_{1-4}$ alkylsulfinyl, $C_{1-10}$ haloalkyl, amino, $C_{1-6}$ acylamino, $C_{1-30}$ alkylamino, di-$C_{1-4}$ alkylamino, $C_{1-5}$ acyl, benzoyl, and five- or six-membered heterocyclic groups which contain 1 to 4 heteroatoms selected from oxygen, sulfur or nitrogen atoms and which are optionally substituted by 1 to 4 substituents selected from the group consisting of a halogen atom and a $C_{1-4}$ alkyl group; or
  2) a five- or six-membered heterocyclic group which contains 1 to 4 heteroatoms selected from oxygen, sulfur or nitrogen atoms and which is optionally substituted with a substituent selected from the group consisting of a halogen atom and a $C_{1-4}$ alkyl group;
- $R^3$ is
  1) a hydrogen atom;
  2) an alkyl group which is optionally substituted with $C_{1-5}$ alkoxycarbonyl;
  3) an acyl group;
  4) an alkoxycarbonyl group;
  5) a phenoxycarbonyl group; or
  6) a carbamoyl group which is optionally substituted with a substituent selected from the group consisting of $C_{1-5}$ alkyl, di-$C_{1-5}$ alkyl, and three- or seven-membered cyclic groups; and
- a and b are each independently 0 or 1.

15. The hair promoting or stimulating method as claimed in claim 14, wherein $R^1$ is a $C_{1-30}$ hydrocarbon group selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ groups.

16. The hair promoting or stimulating method as claimed in claim 14, wherein $R^2$ is a $C_{1-30}$ hydrocarbon group substituted by amino, $C_{1-6}$ acylamino, $C_{1-30}$ alkylamino, di-$C_{1-4}$ alkylamino, or five- or six-membered heterocyclic groups which contain 1 to 4 heteroatoms selected from oxygen, sulfur or nitrogen atoms and which is optionally substituted by 1 to 4 substituents selected from the group consisting of a halogen atom and a $C_{1-4}$ alkyl group, wherein said $C_{1-30}$ hydrocarbon group is selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups.

17. The hair promoting or stimulating method as claimed in claim 14, wherein $R^2$ is a group of the formula

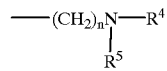

wherein $R^4$ and $R^5$ are each independently a hydrogen atom or a $C_{1-5}$ alkyl group which is optionally substituted by hydroxyl, and n is an integer of 1 to 10.

18. The hair promoting or stimulating method as claimed in claim 14, wherein the compound of formula (I) is a compound selected from the group consisting of:

2,2-dimethyl-3-{[(octadecylamino)carbonyl]-oxy}propyl N-[3-(dimethylamnino)propyl]carbamate or a salt thereof;

2,2-dimethyl-3-{[(octadecylamino)carbonyl]-oxy}propyl N-[(2-piperidinoethyl)carbamate or a salt thereof;

2,2-dimethyl-3-[[[(3-morpholinopropyl)amino]-carbonyl]oxy]propyl N-octadecylcarbamate or a salt thereof;

2,2-dimethyl-3-{[(octadecylamino)carbonyl]-oxy}propyl N-[3-(diethylamino)propyl]carbamate or a salt thereof;

2,2-dimethyl-3-{[(octadecylamino)carbonyl]-oxy}propyl 4-methyltetrahydro-1(2H)-pyrazinecarboxylate or a salt thereof;

2,2-dimethyl-3-(octadecyloxy)propyl N-[3-(dimethylamino)propyl]carbamate or a salt thereof; and 2,2-dimethyl-3-(octadecyloxy)propyl N-(3-morpholinopropyl)carbamate or a salt thereof.

19. A method of promoting hair growth in a mammal which comprises topically applying an effective amount of a compound of the following formula (I), or a pharmaceutically or cosmetically acceptable salt thereof, to the skin or hair of a mammal requiring a hair promotion treatment:

Formula (I):

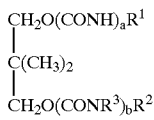

wherein
- $R^1$ and $R^2$ are each independently:
  1) a $C_{1-30}$ hydrocarbon group which is optionally substituted, said $C_{1-30}$ hydrocarbon group is selected from the group consisting of $C_{1-30}$ alkyl, $C_{3-8}$ cycloalkyl, $C_{2-10}$ alkenyl, $C_{2-10}$ alkynyl, $C_{3-10}$ cycloalkenyl, $C_{6-14}$ aryl and $C_{7-16}$ aralkyl groups, wherein when the $C_{1-30}$ hydrocarbon group is substituted, the substituents are one to five substituents selected from the group consisting of halogen, hydroxyl, mercapto, oxo, thioxo, cyano, carbamoyl, carboxyl, $C_{1-4}$ alkoxycarbonyl, sulfo, $C_{1-4}$ alkoxy, phenoxy, halogenophenoxy, $C_{1-4}$ alkylthio, phenylthio, $C_{1-4}$ alkylsulfinyl, $C_{1-10}$ haloalkyl, amino, $C_{1-6}$ acylamino, $C_{1-30}$ alkylamino, di-$C_{1-4}$ alkylamino, $C_{1-5}$ acyl, benzoyl, and five- or six-membered heterocyclic groups which contain 1 to 4 heteroatoms selected from oxygen, sulfur or nitrogen atoms and which are optionally substituted by 1 to 4 substituents selected from the group consisting of a halogen atom and a $C_{1-4}$ alkyl group; or 2) a five- or six-membered heterocyclic group which contains 1 to 4 heteroatoms selected from oxygen, sulfur or nitrogen atoms and which is optionally substituted with a substituent selected from the group consisting of a halogen atom and a $C_{1-4}$ alkyl group;

$R^3$ is
1) a hydrogen atom;
2) an alkyl group which is optionally substituted with $C_{1-5}$ alkoxycarbonyl;
3) an acyl group;
4) an alkoxycarbonyl group;
5) a phenoxycarbonyl group; or
6) a carbamoyl group which is optionally substituted with a substituent selected from the group consisting of $C_{1-5}$ alkyl, di-$C_{1-5}$ alkyl, and three- or seven-membered cyclic groups; and a and b are each independently 0 or 1.

* * * * *